(12) United States Patent
Park et al.

(10) Patent No.: US 8,943,886 B2
(45) Date of Patent: Feb. 3, 2015

(54) ORTHODONTIC FORCE-MEASURING DEVICE USING A TYPODONT AND A LOAD CELL

(71) Applicant: University-Industry Cooperation Group of Kyung Hee University, Yongin (KR)

(72) Inventors: Hun Kuk Park, Seoul (KR); Sam Jin Choi, Seoul (KR); Ki Ho Park, Seoul (KR); Sung Hoon Lee, Seoul (KR); You Jin Cheong, Seoul (KR); Ok Kyun Kim, Seoul (KR); Hyun Jong Cho, Daejeon (KR); Sung Vin Yim, Seoul (KR)

(73) Assignee: University-Industry Cooperation Group of Kyung Hee University, Yongin-Si (KR)

( * ) Notice: Subject to any disclaimer, the term of this patent is extended or adjusted under 35 U.S.C. 154(b) by 0 days.

(21) Appl. No.: 14/346,491

(22) PCT Filed: Sep. 26, 2012

(86) PCT No.: PCT/KR2012/007778
§ 371 (c)(1),
(2) Date: Mar. 21, 2014

(87) PCT Pub. No.: WO2013/048124
PCT Pub. Date: Apr. 4, 2013

(65) Prior Publication Data
US 2014/0227652 A1    Aug. 14, 2014

(30) Foreign Application Priority Data

Sep. 26, 2011   (KR) ........................ 10-2011-0097150

(51) Int. Cl.
   *A61B 5/00*   (2006.01)
   *A61C 19/04*  (2006.01)
   *A61C 7/02*   (2006.01)
   *A61C 7/00*   (2006.01)

(52) U.S. Cl.
   CPC . *A61C 19/04* (2013.01); *A61C 7/02* (2013.01); *A61C 7/00* (2013.01)
   USPC .......................................................... 73/172

(58) Field of Classification Search
   USPC .......................................................... 73/172
   See application file for complete search history.

(56) References Cited

U.S. PATENT DOCUMENTS

| 3,900,953 | A * | 8/1975 | Posen .............................. 433/72 |
| 6,120,287 | A * | 9/2000 | Chen ................................ 433/2 |
| 2009/0030347 | A1 * | 1/2009 | Cao ............................... 600/590 |

FOREIGN PATENT DOCUMENTS

| JP | 06-304183 A | 11/1994 |
| KR | 101201176 B1 | 11/2012 |

OTHER PUBLICATIONS

International Search Report, mailed Mar. 25, 2013, for PCT/KR2012/007778, 2 pages.

*Primary Examiner* — Lisa Caputo
*Assistant Examiner* — Jamel Williams
(74) *Attorney, Agent, or Firm* — Seed IP Law Group PLLC

(57) ABSTRACT

The present invention relates to an orthodontic force measuring device using a typodont and a load cell, and more particularly, to an orthodontic force measuring device using a typodont and a load cell, which connects an orthodontic application wire to a typodont, employs a load cell to measure an orthodontic force, reduces measurement error which may occur in a measurement method based on an image, precisely measures an orthodontic force, and measures an orthodontic force in a three-dimensional manner.

6 Claims, 15 Drawing Sheets

US 8,943,886 B2

ORTHODONTIC FORCE-MEASURING DEVICE USING A TYPODONT AND A LOAD CELL

TECHNICAL FIELD

The present invention relates to an orthodontic force measuring device using a typodont and a load cell, and more particularly, to an orthodontic force measuring device using a typodont and a load cell, which connects an orthodontic force application wire to a typodont and employs a load cell to reduce measurement error which may occur in measurement methods based on the image, and measures an orthodontic force in a three-dimensional manner.

BACKGROUND ART

In general, orthodontic treatment is performed in such a manner as to control an orthodontic appliance in a suitable position and direction, in order to move the entire teeth to be straight in a desired direction. For the movement, a plurality of brackets are installed on the teeth or band, and a wire for tooth correction is coupled to connect the plurality of brackets.

At this time, restoration force caused by the elasticity of the tooth correction wire is used to apply an orthodontic force, such as push, pull, or twist, to the teeth of a patient. Then, the teeth may be moved relative to one another.

As one treatment method of the above-described relative-movement orthodontic treatments, buccal-surface orthodontics may be used. However, when a patient wears such en orthodontic appliance, the orthodontic appliance may significantly influence the patient's daily life, thereby applying serious mental stress to the patient.

Furthermore, during such an orthodontic treatment, a tooth behind the canines may have to be extracted due to various reasons, and the entire front teeth including the canine may have to be towed to the rear. In order to move the front teeth to the rear while the arrangement of the front teeth are maintained as they originally were, a force must be applied to the center of resistance of the teeth.

The center of resistance refers to a point to which a force is applied to move a tooth planted in a hard bone, such that the tooth does not fall over. In general, the center of resistance of a front tooth is positioned between ⅓ and ½ of the distance from the ridge to the root of the tooth.

However, since an orthodontic appliance is attached on the teeth and a tooth correction wire is coupled to the orthodontic appliance, the point to which a force is applied is inevitably located at a lower position than the center of resistance at all times. In general, the center of resistance exists at a distance of about 10 mm above the position at which a bracket is attached. Thus, a force cannot be applied to the buccal surface from the center of resistance due to the structure of the oral cavity.

According to a recent orthodontic treatment, a tooth correction wire called a lever arm is installed on a lingual bracket, a soldering operation is performed to close a space, and a pulling force is applied from a position close to the center of resistance of a tooth to be corrected. When front teeth are towed to the rear during lingual correction, the lever arm is welded to the tooth correction wire for closing the space. Thus, the slope of the teeth may be adjusted according to an operator's intention.

In the above-described orthodontic treatment, however, since the soldering operation is performed, a lot of heat is required. When the heat is applied to the two tooth correction wires, the tooth correction wires may lose elasticity. Then, the tooth correction wires may not normally exhibit an orthodontic force when closing the space.

Hereafter, referring to FIG. 1, an orthodontic force measurement device for solving the above-described problem will be described. The orthodontic force measurement device has been disclosed in Korean Patent Laid-open Publication No. 10-2011-0067553.

The orthodontic force measurement device includes a support unit 10, a vernier caliper 20, an imaging device 30, a tooth correction wire 40, and a plurality of weights 50. The support unit 10 includes a base plate 11, a vernier caliper support part 12, a vernier caliper cover 13, a bracket 14, and an imaging device support part 15. The vernier caliper 20 is positioned at one side of the support unit 10. The imaging device 30 is positioned at the other side of the support unit 10. The tooth correction wire 40 is connected to the support unit 10. The plurality of weights 50 are positioned in the center of the tooth correction wire 40 and have different weights.

The orthodontic force measurement device uses measurement method based on an image obtained through the imaging device 30, which introduces measurement error. Thus, the orthodontic force measurement device cannot precisely measure an orthodontic force.

Furthermore, the orthodontic force measurement device can measure only an orthodontic force in a single direction through the weights 50. Thus, the orthodontic force measurement device cannot measure an orthodontic force in multiple directions.

DISCLOSURE

Technical Problem

The present invention is made by recognizing at least any one of demands or problems which occur in the related art as described above.

An aspect of the present invention provides an orthodontic force measuring device using a typodont and a load cell, which is capable of reducing measurement error which may occur in the conventional measurement method based on an image, when a displacement for an arbitrary orthodontic force is measured.

Another aspect of the present invention provides an orthodontic force measuring device using a typodont and a load cell, which is capable of measuring an orthodontic force in a three-dimensional manner, while the conventional orthodontic force measurement device measures an orthodontic force in a single direction.

Technical Solution

An orthodontic force measuring device using a typodont and a load cell in accordance with an embodiment of the present invention to realize at least one of the above problems may include the following features.

According to one aspect of the present invention, there is provided an orthodontic force measuring device including: a T-shaped rail frame including first and second rail frames; a tooth unit including a support positioned on the first rail frame and a typodont positioned over the support; an orthodontic force application unit positioned over the second rail frame and including a digital push-pull gauge and a support module; an orthodontic force sensing unit connected to an end of the digital push-pull gauge and including a first coupling, a load cell, and a second coupling, which are positioned on a coaxial line; and an orthodontic force application wire connecting the typodont and the first coupling, wherein the typodont is positioned over the support which is moved over the first rail frame, and the digital push-pull gauge measures an orthodontic force applied to the orthodontic force application wire connected to the typodont.

The support module may include: a base having a plurality of base holes formed in a plate member; a central base positioned under the base, and including a plurality of fixing rods protruding to be inserted into the respective base holes and a central base hole formed through the center thereof; a manipulation unit inserted into the central base hole and positioned between the base and the central base; a lower base positioned under the central base and including a lower base groove positioned in the center thereof; and a lower rotating shaft inserted into the lower base groove and positioned between the central base and the lower base.

As the tooth unit is moved to over the first rail frame, the base may be rotated about the manipulation unit.

The orthodontic force measuring device may further include a transport unit including: a rotating shaft connected to the other end of the digital push-pull gauge; a rotating member mounted at one end of the rotating shaft; and a handle connected to one surface of the rotating member. The digital push-pull gauge may be moved to above the second rail frame as the handle is turned.

The digital push-pull gauge may have a measurement range of 0 to 2 kg or 0 to 19.6N, include two measurement modes of a peak value mode and a normal value mode, and have a 24 bit sigma-delta AD converter and an RS-232C output signal mounted therein.

The load cell may be formed of aluminum and plated special steel, the rated output of the load cell may be 1.0 mv/v±10%, a zero balance of the load cell may be ±10% of the rated output, an applied voltage of the load cell may be set in the range of 3V to 5V, input impedance of the load cell is $350\pm10\Omega$, output impedance of the load cell may be $350\pm5\Omega$, a temperature effect on zero balance in the load cell may be ±0.5% of rated output/10° C., and a temperature effect on output in the load cell may fall within ±0.5% of weight/10° C.

Advantageous Effects

In accordance with the embodiment of the present invention, the orthodontic force application wire is connected to the typodont, and the load cell is employed to measure an applied orthodontic force. Thus, when displacement for an arbitrary orthodontic force is measured, measurement error which may occur in an image based measurement method may be reduced, and the orthodontic force may be precisely measured.

As the typodont positioned over the first rail frame is moved left and right, an orthodontic force may be measured in a three-dimensional manner.

MODE FOR INVENTION

Figure 1:
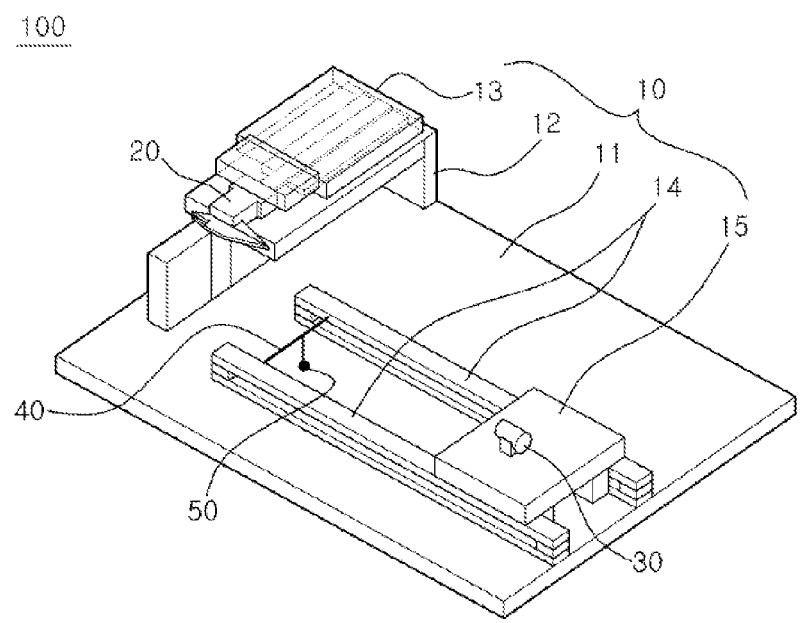
FIG. 1 is a perspective view of a conventional orthodontic force measurement device.
Figure 2:
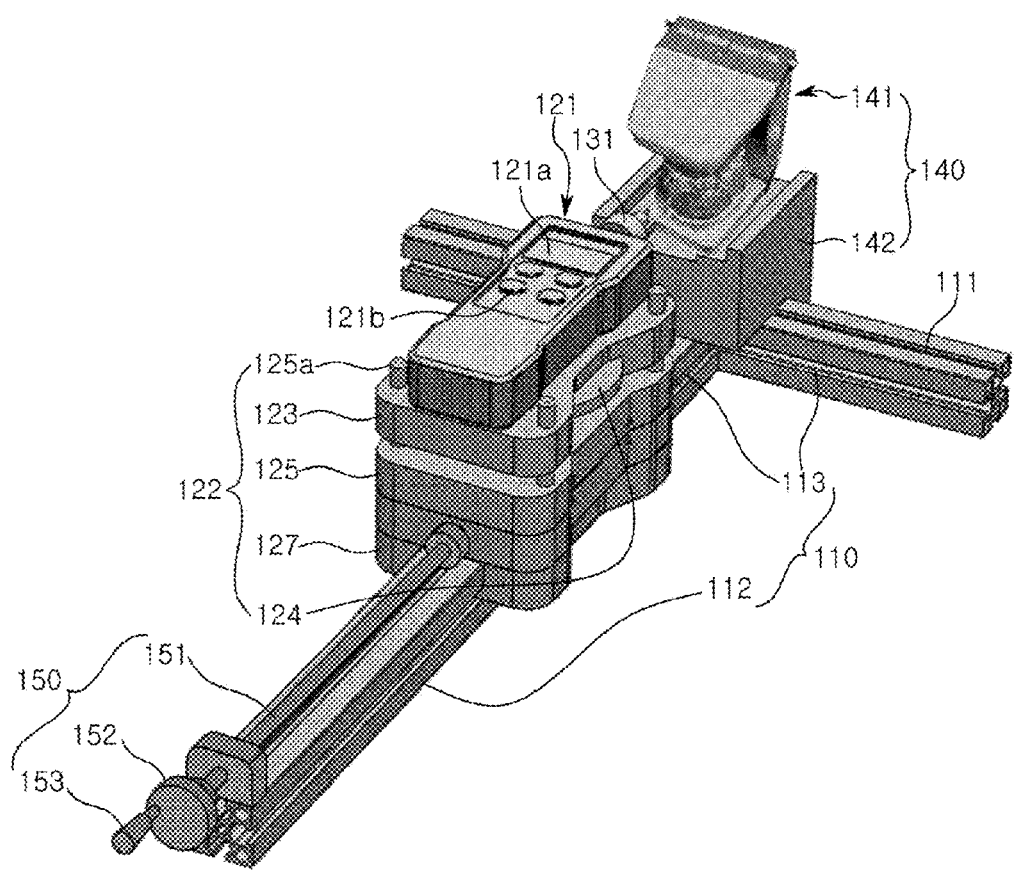
FIG. 2 is a perspective view of an orthodontic force measuring device using a typodont and a load cell in accordance with an embodiment of the present invention.
Figure 3:
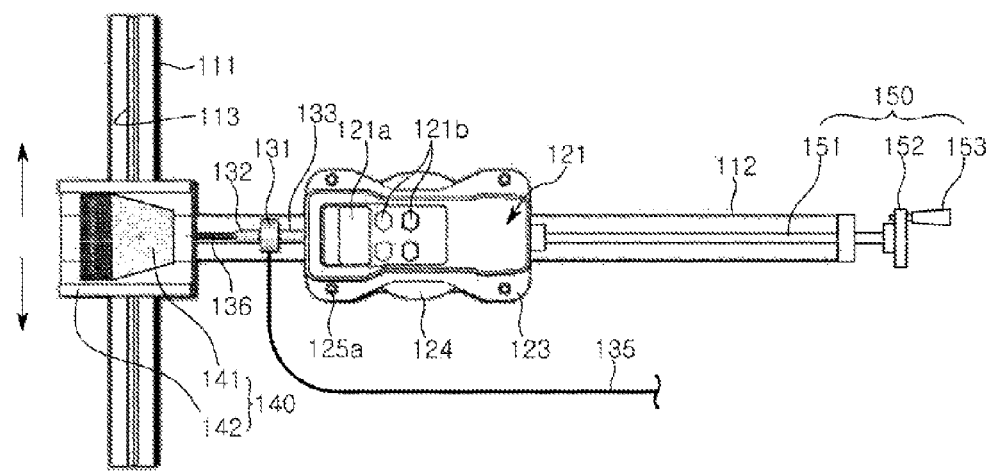
FIG. 3 is a plan view of the orthodontic force measuring device using a typodont and a load cell in accordance with the embodiment of the present invention.
Figure 4:
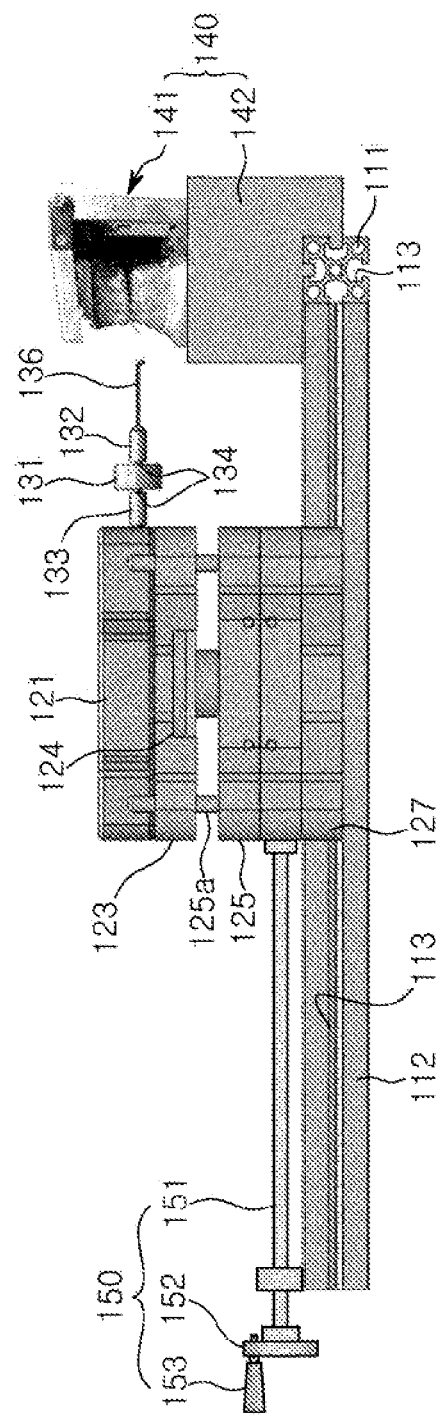
FIG. 4 is a side view of the orthodontic force measuring device using a typodont and a load cell in accordance with the embodiment of the present invention.

Elements of an orthodontic force measuring device 100 using a typodont and a load cell in accordance with an embodiment of the present invention may be integrated or separately provided, if necessary. Furthermore, a part of the element may be omitted depending on a utilization form.

The orthodontic force measuring device 100 using a typodont and a load cell in accordance with the embodiment of the present invention will be described with reference to FIGS. 2 to 15. In the drawings, the thicknesses of lines or the sizes of elements may be exaggerated for clarity of illustration. Furthermore, terms used herein are terms defined in consideration of functions in the present invention, and may differ depending on a user or operator's intention or custom. Thus, the definitions of the terms will be determined on the basis of the contents of the present specification.

Hereafter, the orthodontic force measuring device 100 using a typodont and a load cell in accordance with the embodiment of the present invention will be described with reference to FIGS. 2 to 6.

The orthodontic force measuring device 100 using a typodont and a load cell in accordance with the embodiment of the present invention includes a rail frame 110, an orthodontic force application unit 120, an orthodontic force sensing unit 130, a tooth unit 140, and a transport unit 150.

The rail frame 110 is formed in a T-shape, and includes a first rail frame 111 and a second rail frame 112. The first rail frame 111 has a plurality of rail frame grooves 113 formed thereon, and the second rail frame 112 has a plurality of rail frame grooves 113 formed thereon and is connected to one surface of the first rail frame 111.

The plurality of rail frame grooves 113 are formed on side surfaces of the first rail frame 111 formed of a solid in a longitudinal direction of the first rail frame 111. The first rail frame 111 serves as a path through which a support 142 to be described below is moved onto the first rail frame 111.

The plurality of rail frame grooves 113 are formed on side surfaces of the second rail frame 112 formed of a solid in a longitudinal direction of the second rail frame 112, like the first rail frame 111. The second rail frame 112 serves as a path through which a support module 122 to be described below is moved onto the first rail frame 111.

The rail frame grooves 113 may be formed on four side surfaces of the first and second rail frames 111 and 112, respectively, in the longitudinal direction. The rail frame grooves 113 serve to guide the support module 122 and the support 142 such that the support module 122 and the support 142 do not come off from the first and second rail frames 111 and 112.

The orthodontic force application unit 120 includes a digital push-pull gauge 121 for applying a small orthodontic force and a support module 122 positioned under the digital push-pull gauge 121 so as to support the digital push-pull gauge 121. The orthodontic force application unit 120 is positioned over the second rail frame 112.

The digital push-pull gauge 121 is moved to above the second rail frame 112 as a handle 153 to be described below is turned. Through the above-described system, the digital push-pull gauge 121 measures an orthodontic force applied to an orthodontic force application wire 136 connected to a typodont 141 to be described below.

As for the digital push-pull gauge 121, a gauge such as AFG-2 may be used to apply an extremely small orthodontic force. The digital push-pull gauge 121 has the following representative specifications.

The digital push-pull gauge 121 has a measurement range of 0 to 2 kg or 0 to 19.6N, and includes two measurement modes such as a peak value mode and a normal value mode. Furthermore, the digital push-pull gauge 121 includes a 24-bit sigma-delta AD converter and an RS-232C output signal mounted therein.

The digital push-pull gauge 121 includes a display unit 121a positioned on the top surface of a hollow case (not illustrated) and an input unit 121b positioned adjacent to the display unit 121a.

The display unit 121a is positioned on the top surface of the hollow case, and serves to display an orthodontic force applied from the orthodontic force application wire 136.

The input unit 121b is positioned adjacent to the display unit 121a, and serves to control on/off of the display unit 121a to display an orthodontic force.

The support module 122 includes a base 123, a manipulation unit 124, a central base 125, a lower rotating shaft 126, and a lower base 127. The base 123 has a plurality of base holes 123a formed in a plate member. The manipulation unit 124 is positioned under the base 123. The central base 125 is positioned under the base 123 such that the manipulation unit 124 is inserted into the central base 125. The lower rotating shaft 126 is positioned under the central base 125. The lower base 127 is positioned under the central base 125 such that the lower rotating shaft 126 is inserted into the lower base 127.

Figure 5:
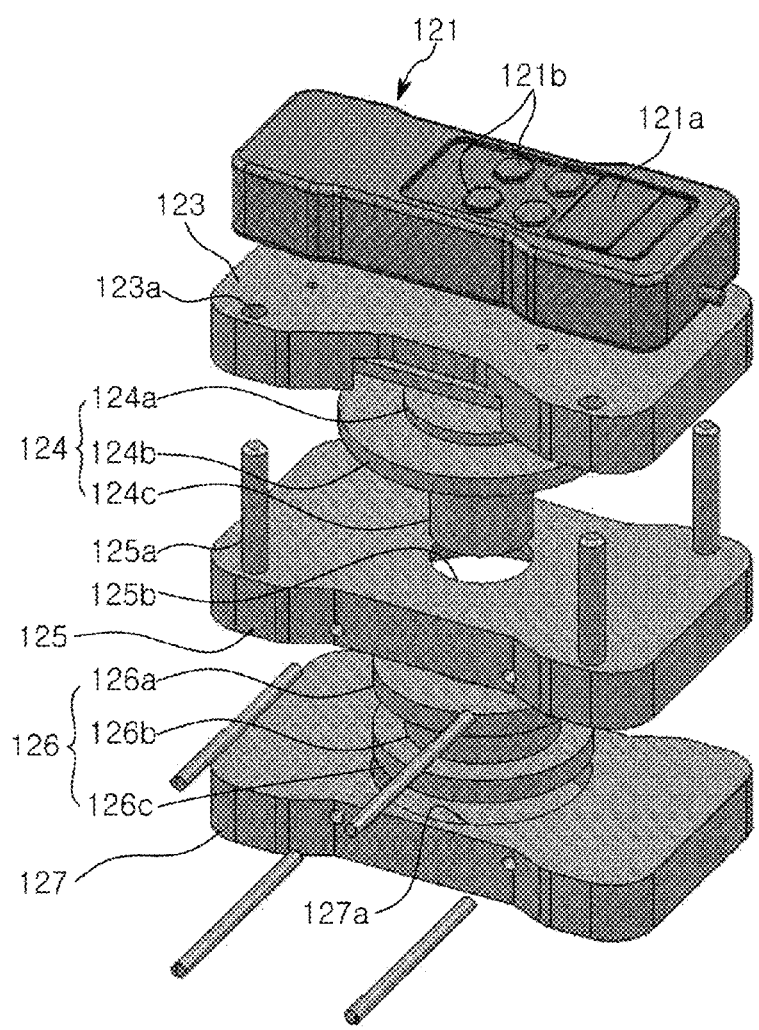
FIG. 5 is an exploded perspective view or an orthodontic force application unit of the orthodontic force measuring device using a typodont and a load cell in accordance with the embodiment of the present invention.
Figure 6:
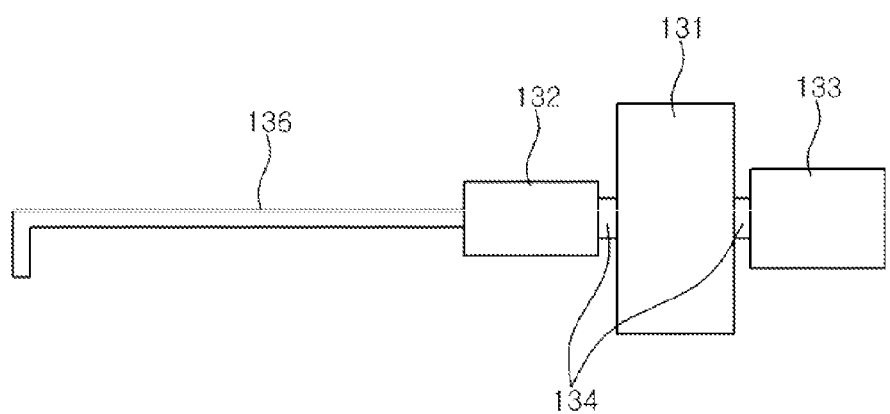
FIG. 6 is a block diagram illustrating an orthodontic force sensing unit of the orthodontic force measuring device using a typodont and a load cell in accordance with the embodiment of the present invention.
Figure 7:
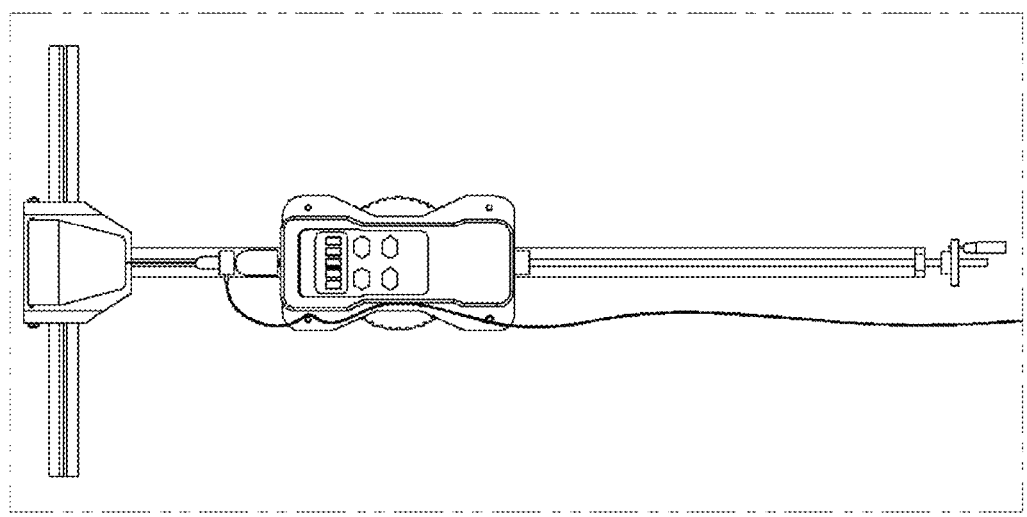
FIG. 7 is a plan view illustrating a prototype of the orthodontic force measuring device using a typodont and a load well in accordance with the embodiment of the present invention.
Figure 8:
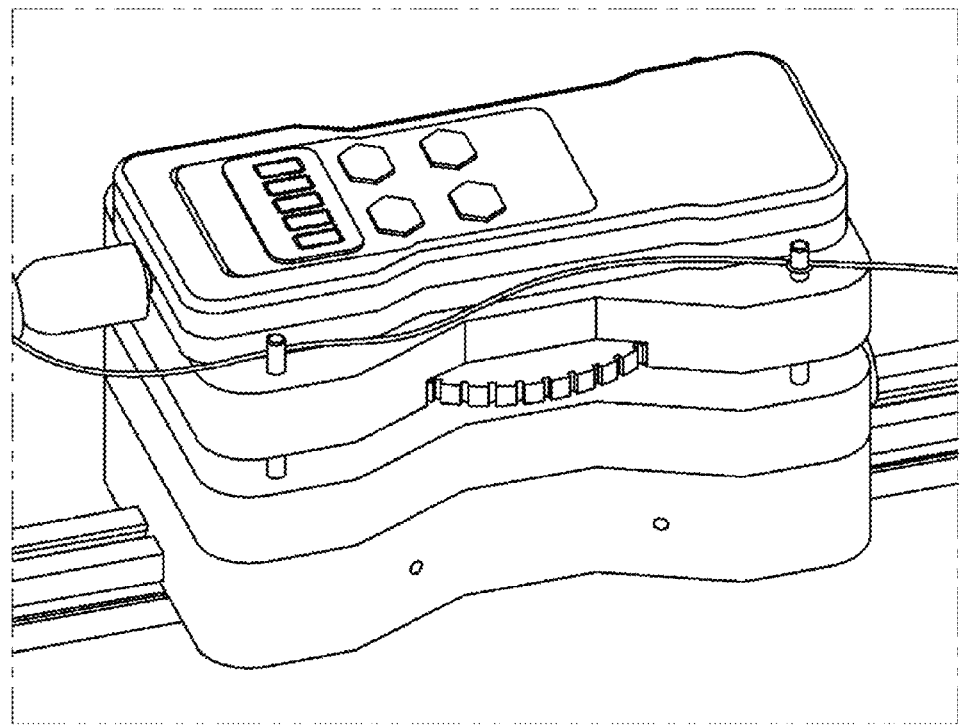
FIG. 8 is a perspective view illustrating the orthodontic force sensing unit and the orthodontic force application unit of the orthodontic force measuring device using a typodont and a load cell in accordance with the embodiment of the present invention.
Figure 9:
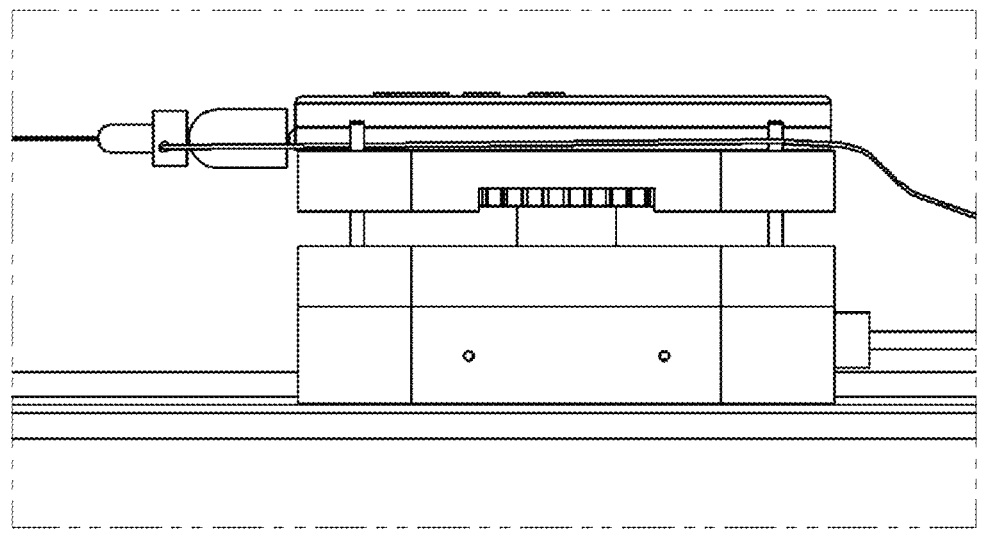
FIG. 9 is a side view illustrating the orthodontic force sensing unit and the orthodontic force application unit of the orthodontic force measuring device using a typodont and a load cell in accordance with the embodiment of the present invention.
Figure 10:
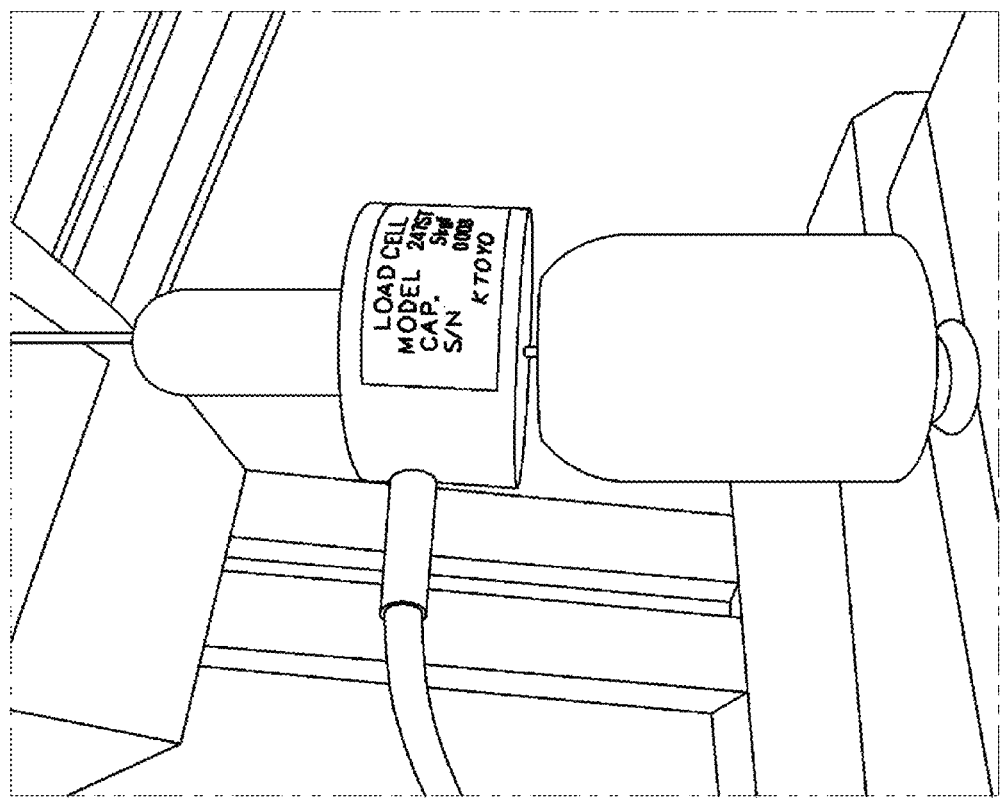
FIG. 10 is a partial detailed diagram illustrating the orthodontic force sensing unit of the orthodontic force measuring device using a typodont and a load cell in accordance with the embodiment of the present invention.
Figure 11:
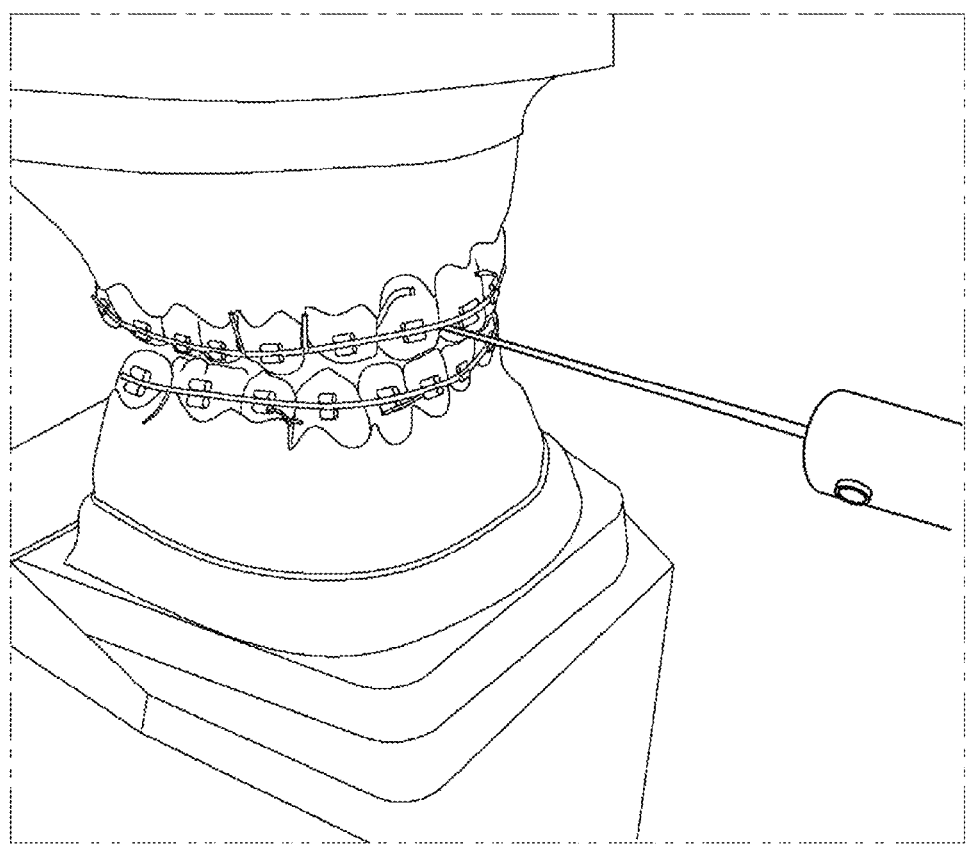
FIG. 11 is a partial detailed diagram illustrating a tooth unit of the orthodontic force measuring device using a typodont and a load cell in accordance with the embodiment of the present invention.
Figure 12:
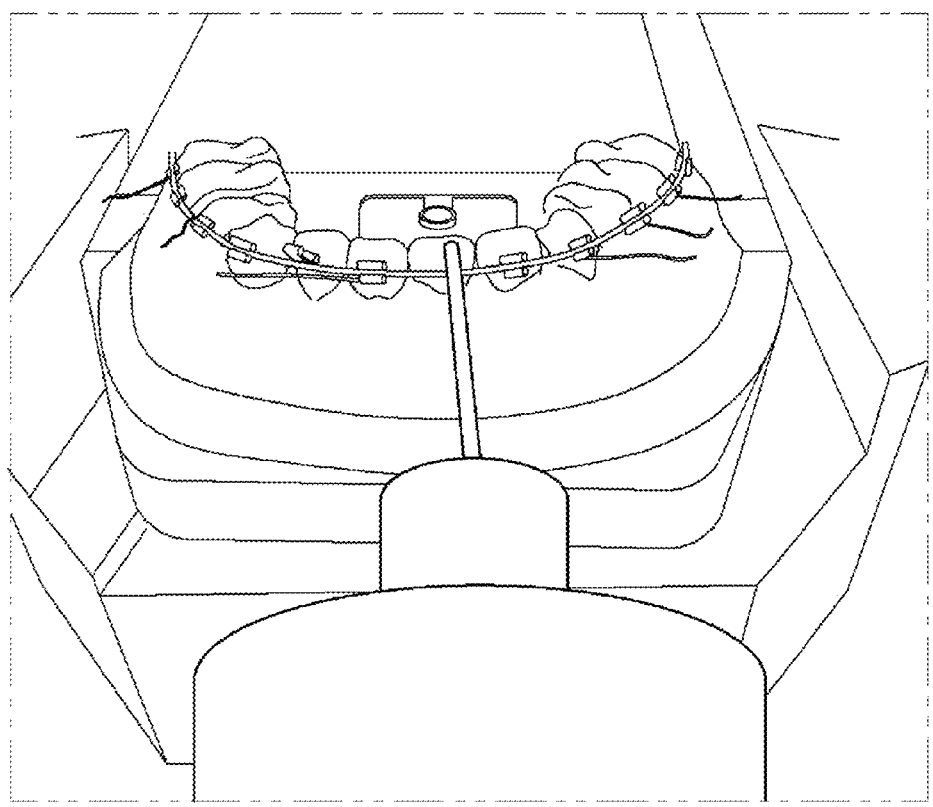
FIG. 12 is a partial detailed diagram illustrating the orthodontic force sensing unit and the tooth unit of the orthodontic force measuring device using a typodont and a load cell in accordance with the embodiment of the present invention.
Figure 13:
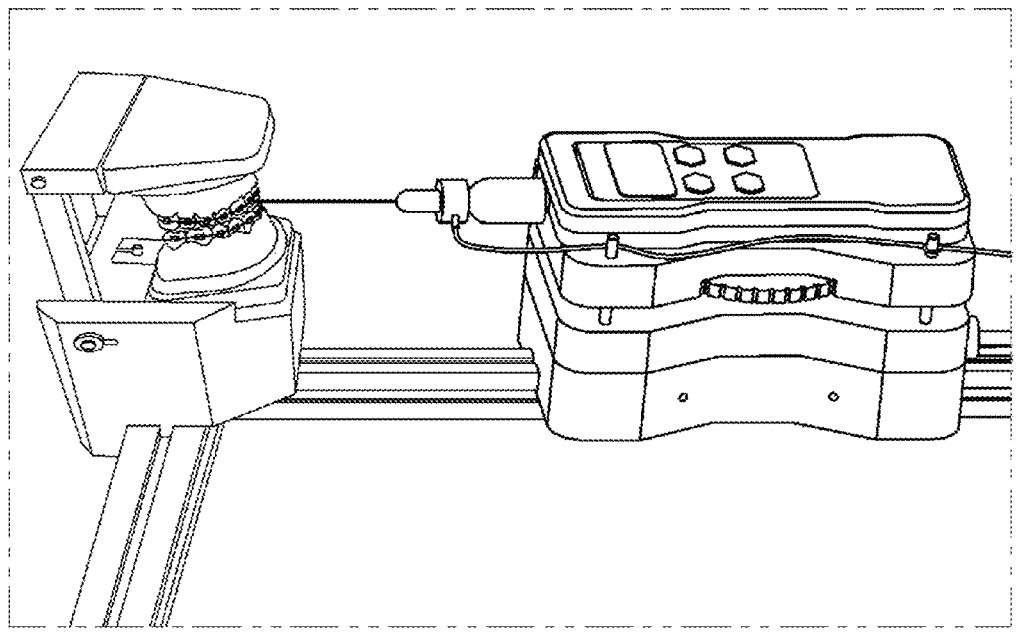
FIG. 13 is a perspective view illustrating that an orthodontic force is applied to a tooth at the front side through the orthodontic force measuring device using a typodont and a load cell in accordance with the embodiment of the present invention.
Figure 14:
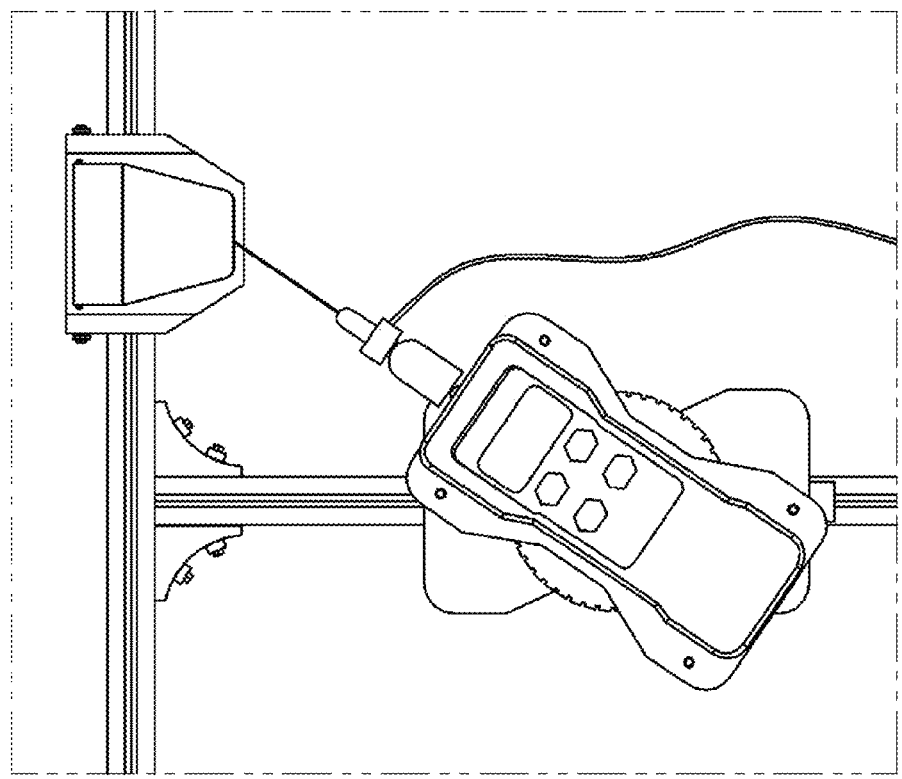
FIG. 14 is a perspective view illustrating that an orthodontic force is applied to a tooth at the left side through the orthodontic force measuring device using typodont and a load cell in accordance with the embodiment of the present invention.
Figure 15:
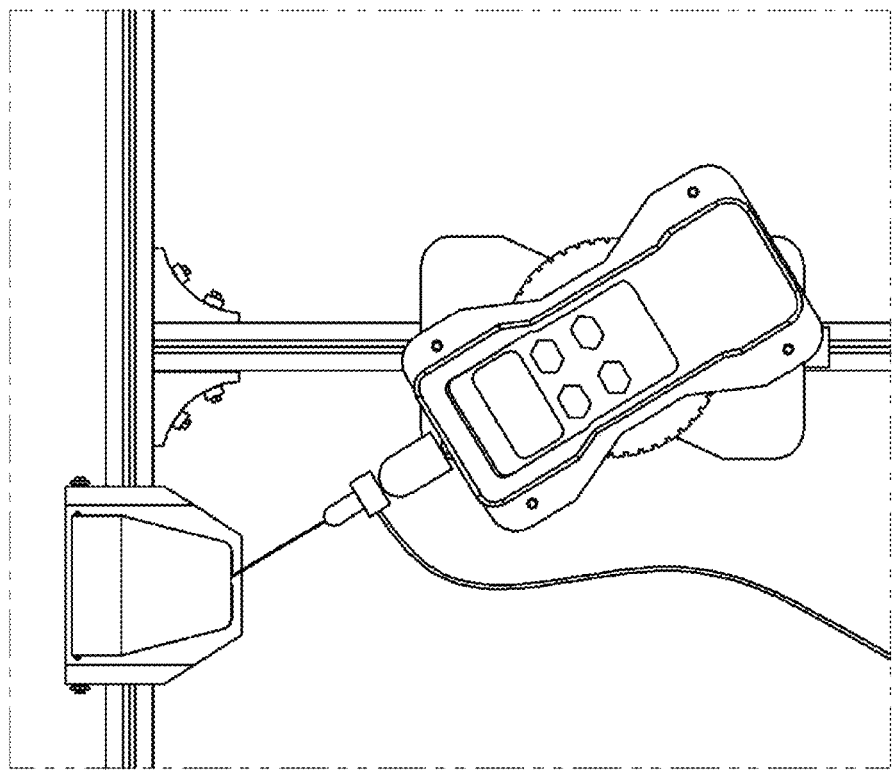
FIG. 15 is a perspective view illustrating that an orthodontic force is applied to a tooth at the right side through the orthodontic force measuring device using a typodont and a load cell in accordance with the embodiment of the present invention.

The base 123 is formed of a plate member, and has the plurality of base holes 123a formed in four corners of the plate member as illustrated in FIG. 5. Since the base 123 may be rotated while supporting the digital push-pull gauge 121, an orthodontic force may be measured in various directions. More specifically, as the tooth unit 140 to be described below is moved to over the first rail frame 111, the base 123 may be rotated about the manipulation unit 124. Thus, an orthodontic force may be measured in various directions.

The manipulation unit 124 is inserted into a central base hole 125b to be described below, and positioned between the base 123 and the central base 125. The manipulation unit 124 includes a first disk 124a, a second disk 124b positioned under the first disk 124a, and a first cylinder 124c positioned under the second disk 124b.

The first disk 124a is formed of a disk-shaped plate member. The first disk 124a may be inserted into a groove (not illustrated) formed in the base 123 and rotated.

The second disk 124b is formed of a disk-shaped plate member, like the first disk 124a. However, the second disk 124b has a larger diameter than that of the first disk 124a, and the bottom surface of the first disk 124a may be connected to the top surface of the second disk 124b such that the first and second disks 124a and 124b are rotated together. The second disk 124b serves to connect and support the first disk 124a and the first cylinder 124c.

The first cylinder 124c has a cylindrical shape opened in a vertical direction. The first cylinder 124c may be inserted into a central base hole 125b to be described below and rotated therein.

The central base 125 is positioned under the base 123, and may have a size corresponding to the base 123. The central base 125 includes a plurality of fixing rods 125a protruding to be inserted into base holes 123a, and the central base hole 125b is formed through the center of the central base 125.

The fixing rods 125a are formed to protrude at a predetermined distance from four corners of one surface of the central base 125, and correspond to the respective base holes 123a. The fixing rods 125a are inserted into the base holes 123a so as to fix the base 123 to the central base 125.

The central base hole 125b is formed through the center of the central base 125, and guides the second disk 124b inserted therein such that the second disk 124b is rotated.

The lower rotating shaft 126 is inserted into the lower base groove 127a to be described below, and positioned between the central base 125 and the lower base 127. The lower rotating shaft 126 includes a third disk 126a, a second cylinder 126b positioned under the third disk 126a, and a fourth disk 126c positioned under the second disk 126b.

The third disk 126a is formed of a disk-shaped plate member, and inserted into a groove (not illustrated) positioned at the bottom of the central base 125.

The second cylinder 126b is also formed of a disk-shaped plate member, but has a small diameter than that of the third disk 126a. The second cylinder 126b serves to connect and support the third and fourth disks 126a and 126c.

The fourth disk 126c is formed to correspond to the third disk 126a, and inserted into the lower base 127 to be described below.

The lower base 127 is formed under the central base 125 and has the same size as the base 123 and the central base 125. The lower base 127 includes a lower base groove 127a positioned in the center thereof.

The lower base groove 127a is formed in the center of the lower base 127, and the lower rotating shaft 126 is inserted into the lower base groove 127a.

The orthodontic force sensing unit 130 is connected to one end of the digital push-pull gauge 121 for measuring a force and displacement, and includes a load cell 131, a first coupling 132, a second coupling 133, a fixed shaft 134, a measurement line 135, and an orthodontic force application wire 136. The load cell 131 serves to measure an orthodontic force. The first coupling 132 is positioned at the front end of the load cell 131. The second coupling 133 is positioned at the rear end of the load cell 131 and formed of polyethylene. The fixed shaft 134 passes through the load cell 131, the first coupling 132, and the second coupling 133. The measurement line 135 is connected to one side of the load cell 131. The orthodontic force application wire 136 is connected to the first coupling 132.

The load cell 131 is used to measure a precise weight, and formed of aluminum and plated special steel. The rated output of the load well 131 is 1.0 mv/v±10%, a zero balance of the load cell 131 is ±10% of the rated output, an applied voltage of the load cell 131 is set in the range of 3V to 5V, input impedance of the load cell 131 is 350±10Ω, output impedance of the load cell 131 is 350±5Ω, a temperature effect on zero balance in the load cell 131 is ±0.5% of rated output/10° C., and a temperature effect on output in the load cell 131 falls within ±0.5% of weight/10° C.

A tensile or compressive force applied to the load cell 131 is transmitted to a high-precision small-sized weight indicator KBS-205. Then, the magnitude of the force applied to the high-precision small-sized weight indicator is displayed as a digital value.

The first coupling 132 is positioned at the front end of the load cell 131 and located on the same line, as the fixed shaft 134. The first coupling 132 is connected to the orthodontic force application wire 136.

The second coupling 133 is positioned at the rear end of the load cell 131, and located on the same line as the fixed shaft 134.

The fixed shaft 134 is formed through the load cell 131, the first coupling 132, and the second coupling 133 so as to connect the load cell 131, the first coupling 132, and the second coupling 133.

The measurement line 135 serves to transmit an orthodontic force measured through the digital push-pull gauge 121 to an external device (not illustrated).

The orthodontic force application wire 136 formed in an L-shape has one end connected to the first coupling 132 and the other end connected to a tooth of a typodont 141 to be described below.

The tooth unit 140 is a tooth-shaped structure, and includes the support 142 positioned over the first rail frame 111 and the typodont 141 positioned over the support 142.

As for the typodont 141, a device used to simulate tooth movement in a orthodontics department of a dental college may be employed so as to increase the possibility of clinical application. The typodont 141 is positioned over the support 142 to be moved over the first rail frame 111.

The support 142 fixes the typodont 141 thereon and is mounted over the T-shaped rail frame 110. Thus, an orthodontic force of a tooth may be measured while the tooth is moved left and right along the rail frame 110.

The transport unit 150 includes a rotating shaft 151, a rotating member 152, and a handle 153. The rotating shaft 151 is connected to the other end of the digital push-pull gauge 121, the rotating member 152 is mounted at one end of the rotating shaft 151, and the handle 153 is connected to one surface of the rotating member 152.

The rotating shaft 151 is connected to the other end of the digital push-pull gauge 121, and connected to the rotating member 152.

The rotating member 152 is mounted at one end of the rotating shaft 151, and connected to the rotating shaft 151 and the handle 153.

The handle 153 is formed to extend a predetermined distance from one surface of the rotating member 152. As a user turns the handle 153, the rotating shaft 151 and the rotating member 152 are rotated. Then, the digital push-pull gauge 121 may be moved over the second rail frame 112.

Hereafter, referring to FIGS. 7 to 15, the operation principle of the orthodontic force measuring device 100 using a typodont and a load cell in accordance with the embodiment of the present invention will be described as follows.

The digital push-pull gauge 121 is mounted on the second rail frame 112 of the T-shaped rail frame 110, and the typodont 141 of the tooth unit 140 is mounted. Then, a laser point is mounted on the orthodontic force application unit 120 so as to take an accurate position of a tooth to be measured, and a measurement position is set.

Then, the orthodontic force sensing unit 130 including the load cell 131, the first coupling 132, the second coupling 133, and she orthodontic force application wire 136 is mounted on the digital push-pull gauge 121 of the orthodontic force application unit 120, the orthodontic force application wire 136 is hooked on the tooth at the measurement position, and the handle 153 positioned at the rear of the orthodontic force application unit 120 is turned to apply an orthodontic force. At this time, the digital push-pull gauge 121 measures the orthodontic force applied through the orthodontic force application wire 136.

As the tooth unit 120 is moved left and right over the first rail frame 111, the orthodontic force may be measured at various angles.

While the present invention has been described with respect to the specific embodiments, it will be apparent to those skilled in the art that various changes and modifications may be made without departing from the spirit and scope of the invention as defined in the following claims.

The invention claimed is:

1. An orthodontic force measuring device comprising:
   a T-shaped rail frame comprising first and second rail frames;
   a tooth unit comprising a support positioned on the first rail frame and a typodont positioned over the support;
   an orthodontic force application unit positioned over the second rail frame and comprising a digital push-pull gauge and a support module;
   an orthodontic force sensing unit connected to an end of the digital push-pull gauge and comprising a first coupling, a load cell, and a second coupling, which are positioned on a coaxial line; and
   an orthodontic force application wire connecting the typodont and the first coupling,
   wherein the typodont is positioned over the support which is moved over the first rail frame, and
   the digital push-pull gauge measures an orthodontic force applied to the orthodontic force application wire connected to the typodont.

2. The orthodontic force measuring device of claim 1, wherein the support module comprises:
a base having a plurality of base holes formed in a plate member;
a central base positioned under the base, and comprising a plurality of fixing rods protruding to be inserted into the respective base holes and a central base hole formed through the center thereof;
a manipulation unit inserted into the central base hole and positioned between the base and the central base;
a lower base positioned under the central base and comprising a lower base groove positioned in the center thereof; and
a lower rotating shaft inserted into the lower base groove and positioned between the central base and the lower base.

3. The orthodontic force measuring device of claim 2, wherein as the tooth unit is moved to over the first rail frame, the base is rotated about the manipulation unit.

4. The orthodontic force measuring device of claim 1, further comprising a transport unit comprising:
a rotating shaft connected to the other end of the digital push-pull gauge;
a rotating member mounted at one end of the rotating shaft; and
a handle connected to one surface of the rotating member, wherein the digital push-pull gauge is moved to above the second rail frame as the handle is turned.

5. The orthodontic force measuring device of claim 1, wherein the digital push-pull gauge has a measurement range of 0 to 2 kg or 0 to 19.6N, comprises two measurement modes of a peak value mode and a normal value mode, and has a 24 bit sigma-delta AD converter and an RS-232C output signal mounted therein.

6. The orthodontic force measuring device of claim 1, wherein the load cell is formed of aluminum and plated special steel, the rated output of the load cell is 1.0 mv/v±10%, a zero balance of the load cell is ±10% of the rated output, an applied voltage of the load cell is set in the range of 3V to 5V, input impedance of the load cell is $350\pm10\Omega$, output impedance of the load cell is $350\pm5\Omega$, a temperature effect on zero balance in the load cell is ±0.5% of rated output/10° C., and a temperature effect on output in the load cell falls within ±0.5% of weight/10° C.

* * * * *